US009848884B2

(12) United States Patent
Bertollo et al.

(10) Patent No.: US 9,848,884 B2
(45) Date of Patent: Dec. 26, 2017

(54) DIVERTICULA REMOVAL CLAMP (71) Applicant: Empire Technology Development LLC, Wilmington, DE (US)

(72) Inventors: Nicky Bertollo, Wollstonecraft (AU); William R. Walsh, Maroubra (AU); Matthew H. Pelletier, Maroubra (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 473 days.

(21) Appl. No.: 14/125,929

(22) PCT Filed: Jan. 10, 2013

(86) PCT No.: PCT/US2013/021071
§ 371 (c)(1),
(2) Date: Jul. 12, 2014

(87) PCT Pub. No.: WO2014/109751
PCT Pub. Date: Jul. 17, 2014

(65) Prior Publication Data
US 2014/0343587 A1 Nov. 20, 2014

(51) Int. Cl.
*A61B 17/122* (2006.01)
*A61B 1/31* (2006.01)
(Continued)

(52) U.S. Cl.
CPC .............. *A61B 17/122* (2013.01); *A61B 1/31* (2013.01); *A61B 17/11* (2013.01);
(Continued)

(58) Field of Classification Search
CPC ... A61B 17/122; A61B 17/11; A61B 17/1114; A61B 1/31; A61B 2017/00004;
(Continued)

(56) References Cited

U.S. PATENT DOCUMENTS 4,808,171 A * 2/1989 Berger .................. A61F 11/002
604/264
5,018,872 A * 5/1991 Suszynski ................. G01J 5/04
374/121
(Continued)

FOREIGN PATENT DOCUMENTS

EP          0469524 B1     9/1996
WO         03026516 A1     4/2003
WO       2008130750 A1    10/2008

OTHER PUBLICATIONS

International Search Report and Written Opinion for PCT/US2013/021071, filed Jan. 10, 2013, dated Mar. 2013.
(Continued)

*Primary Examiner* — Julian W Woo
(74) *Attorney, Agent, or Firm* — Turk IP Law, LLC (57) ABSTRACT

Technologies are generally provided for a tissue removal device for removing tissue protrusions extending from a wall of intestines. The tissue removal device may be a bell shaped tube configured to slide over an inflamed diverticulum that has been inverted to extend into interior space of the colon. The tissue removal device run be slid over the inverted diverticulum with a portion of the tissue removal device having a widest diameter oriented near the colon wall and a portion having a narrowest diameter oriented near a tip of the diverticulum. A pressure gradient may be induced along the walls of the tissue removal device such that the point of highest pressure at the narrowest opening may cause the walls of the diverticulum to be pinched together to induce necrosis and removal of the diverticulum, while promoting healing of the colon walls over the region of decreasing pressure.

20 Claims, 11 Drawing Sheets (51) Int. Cl.
*A61B 17/11* (2006.01)
*A61B 17/00* (2006.01)
*A61B 17/30* (2006.01)

(52) U.S. Cl.
CPC . *A61B 17/1114* (2013.01); *A61B 2017/00004* (2013.01); *A61B 2017/1117* (2013.01); *A61B 2017/1121* (2013.01); *A61B 2017/1142* (2013.01); *A61B 2017/306* (2013.01)

(58) Field of Classification Search
CPC ..... A61B 2017/1117; A61B 2017/1121; A61B 2017/1142; A61B 2017/306
See application file for complete search history.

(56) References Cited

U.S. PATENT DOCUMENTS

| | | | | |
|---|---|---|---|---|
| 5,100,419 | A * | 3/1992 | Ehlers | A61B 17/0057 606/140 |
| 5,209,754 | A * | 5/1993 | Ahluwalia | A61B 17/0218 600/207 |
| 5,224,497 | A | 7/1993 | Ehlers | |
| 5,392,764 | A * | 2/1995 | Swanson | A61B 1/32 600/187 |
| 9,314,556 | B2 * | 4/2016 | Tuseth | A61B 17/3478 |
| 2007/0051375 | A1 * | 3/2007 | Milliman | A61B 17/3423 128/856 |
| 2008/0039864 | A1 * | 2/2008 | Feuer | A61B 17/4241 606/119 |
| 2008/0135053 | A1 * | 6/2008 | Gruber | A61B 17/12022 128/831 |
| 2009/0105728 | A1 * | 4/2009 | Noda | A61B 17/12013 606/139 |
| 2011/0190783 | A1 * | 8/2011 | Calderon | A61B 17/4241 606/119 |
| 2012/0059394 | A1 | 3/2012 | Brenner et al. | |
| 2014/0200398 | A1 * | 7/2014 | Hawkins | A61B 17/0469 600/37 |

OTHER PUBLICATIONS

"O-ring," accessed at https://web.archive.org/web/20121013232919/http://en.wikipedia.org/wiki/O-ring, last modified on Oct. 1, 2012, pp. 8.

* cited by examiner

DIVERTICULA REMOVAL CLAMP

CROSS-REFERENCE TO RELATED APPLICATION

This Application is the U.S. National Stage filing under 35 U.S.C. §371 of International Application No. PCT/US2013/021071 filed on Jan. 10, 2013.

BACKGROUND

Unless otherwise indicated herein, the materials described in this section are not prior art to the claims in this application and are not admitted to be prior art by inclusion in this section.

Diverticulitis is a condition in which muscle tissue of the colon and intestines bulges out into the peritoneal cavity forming a tissue protrusion called a diverticulum. Diverticula can also form due to muscle weakness within the colon walls, which may cause the colon muscle tissue to separate and allow parts of the inner mucosal membrane to be pushed out into the peritoneal space as a tissue protrusion or diverticulum. Diverticula can also occur in other anatomical structures, such as the esophagus, duodenum, bladder, and heart, as a few examples.

Diverticula can become inflamed and infected due to entrapped fecal matter and bacterial growth, which may cause mild to severe symptoms in individuals. Treatment of the systems may often require invasive surgery in order to remove the inflamed diverticula and segments or portions of the intestines where the diverticula are located.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

The present disclosure generally describes a tissue removal device for removing tissue protrusions extending from a wall of intestines. The tissue removal device may include a tube including a first opening having a first diameter, and a second opening having a second diameter, the tube being configured to slide over a tissue protrusion such that the first opening may be adjacent to the wall of the colon and the tissue protrusion passes through the second opening, wherein the tube may have a tapered shape extending from the first opening to the second opening.

According to other embodiments, the present disclosure also describes a method of removing tissue protrusions extending from a wall of intestines. The method may include inverting one or more tissue protrusions extending from the wall of the intestines such that the tissue protrusions extend into an interior space of the intestines, providing a tube configured to slide over a tissue protrusion such that a first opening of the tube having a first inner diameter may be adjacent to the wall of the intestines, and the tissue protrusion passes through a second opening of the tube having a second inner diameter, wherein the tube may have a tapered shape extending from the first opening to the second opening; and causing opposing muscularis mucosal walls of the tissue protrusion located within the second opening to bond for promoting necrosis and removal of the tissue protrusions.

According to further embodiments, the present disclosure describes a system for removing tissue protrusions extending from a wall of intestines. The system may include a surgical delivery tool for providing access to an interior space of the intestines, and a tube including a first opening having a first diameter, and a second opening having a second diameter, the tube being configured to slide over a tissue protrusion such that the first opening may be adjacent to the wall of the colon and the tissue protrusion passes through the second opening, wherein the tube may have a tapered shape extending from the first opening to the second opening.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter cilia, to compositions, methods, apparatus, systems, and/or devices related to providing a device for removing diverticula from the colon.

Briefly stated, technologies are generally provided for a tissue removal device for removing tissue protrusions extending from a wall of intestines. The tissue removal device may be a bell shaped tube configured to slide over an inflamed diverticulum that has been inverted to extend into interior space of the colon. The tissue removal device may be slid over the inverted diverticulum with a portion of the tissue removal device having a widest diameter oriented near the colon wall and a portion having a narrowest diameter oriented near a tip of the diverticulum. A pressure gradient may be induced along the walls of the tissue removal device such that the point of highest pressure at the narrowest opening may cause the walls of the diverticulum to be pinched together to induce necrosis and removal of the diverticulum, while promoting healing of the colon walls over the region of decreasing pressure.

Figure 1:
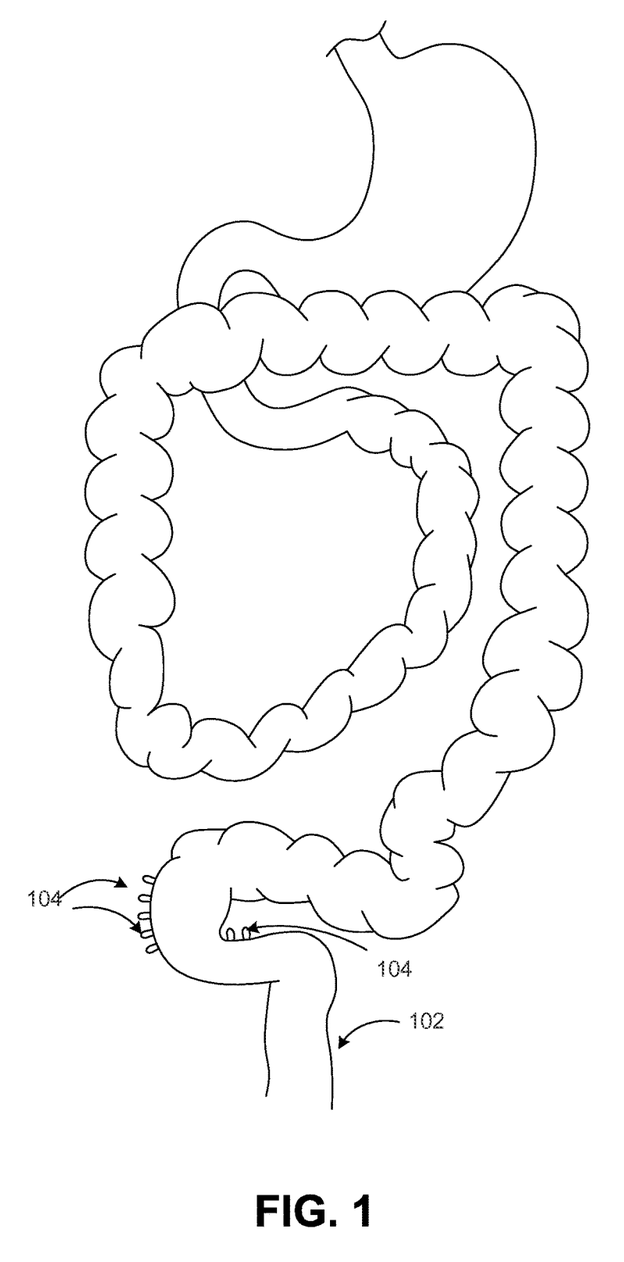
FIG. 1 illustrates an example anatomical layout of the intestines with diverticula.

FIG. 1 illustrates an example anatomical layout of the intestines with diverticula, arranged in accordance with at least some embodiments as described herein. Diverticula 104 may form on outer surfaces of the colon 102. Diverticula 104 are protrusions or outpocketings of colonic mucosa and submucosa tissue that may form due to weaknesses of muscle layers in the colon wall. Diverticula 104 may also form in other anatomical structures such as the esophagus, blood vessels, bladder, heart, urethra, and the heart to name a few examples. When diverticula 104 form in the colon 102 can become infected and inflamed, which may cause painful and uncomfortable symptoms. When diverticula 104 become inflamed, one may be diagnosed with diverticulitis, and inflamed diverticula 104 may be removed to prevent and treat diverticulitis in order to relieve painful and uncomfortable symptoms.

Figure 2:
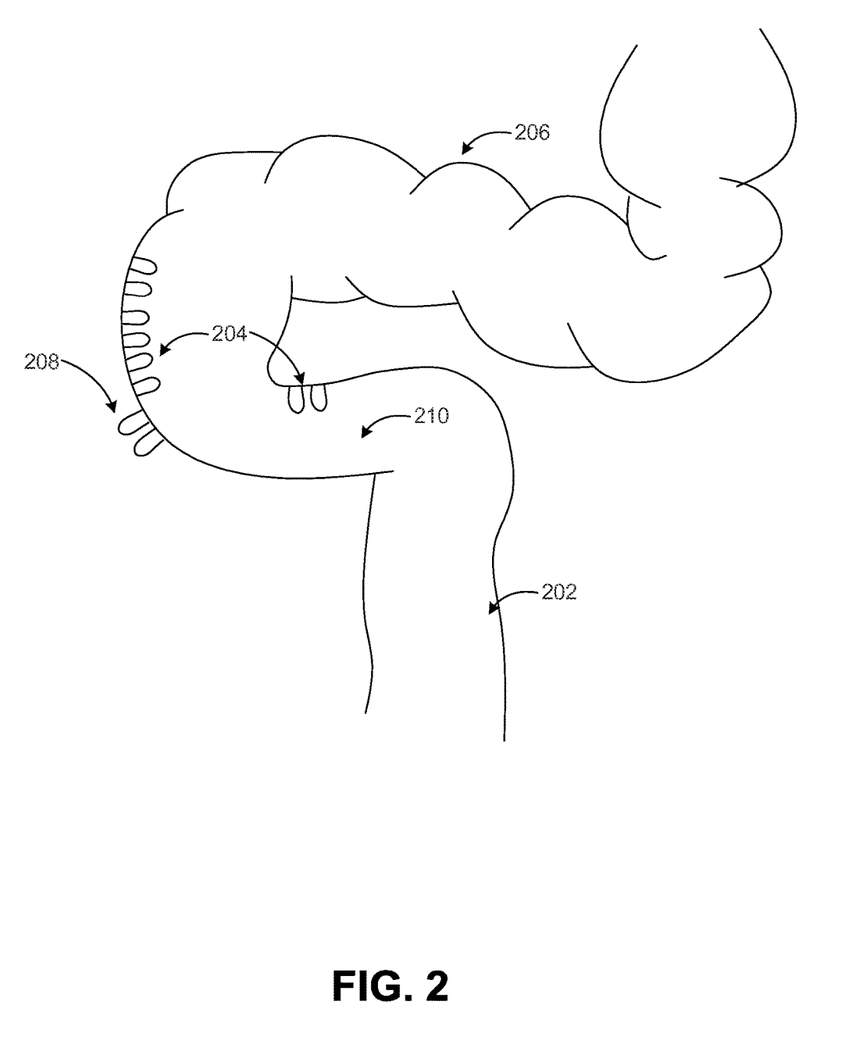
FIG. 2 illustrates an example anatomical layout of the intestines with inverted diverticula.

FIG. 2 illustrates an example anatomical layout of the intestines with inverted diverticula, arranged in accordance with at least some embodiments as described herein. As previously described, when diverticula form in the colon 206, the diverticula may be removed to prevent and treat diverticulitis symptoms. Diverticula typically form as outpocketings 208 of the colonic muscle, and occasionally, in some cases, diverticula can protrude into the lumen or an interior space 210 of the colon as inverted diverticula.

In an example embodiment, when diverticula need to be removed, if the diverticula are present as outpocketings 208, the diverticula may be inverted such that the diverticula may extend into an interior space 210 of the colon 206 as inverted diverticula 204. Inverting the diverticula into the interior space of the colon may enable the inverted diverticula 204 to be removed employing an endoscopic procedure. The endoscopic procedure may enable access to the inverted diverticula 204 via the rectum 202 and the colon 206 so that the inverted diverticula can be removed without requiring major invasive surgery. Similarly, the endoscopic procedure may enable access to diverticula located in other anatomical structures through other natural orifices, such as the mouth, for example for accessing esophageal diverticula.

Figure 3A:
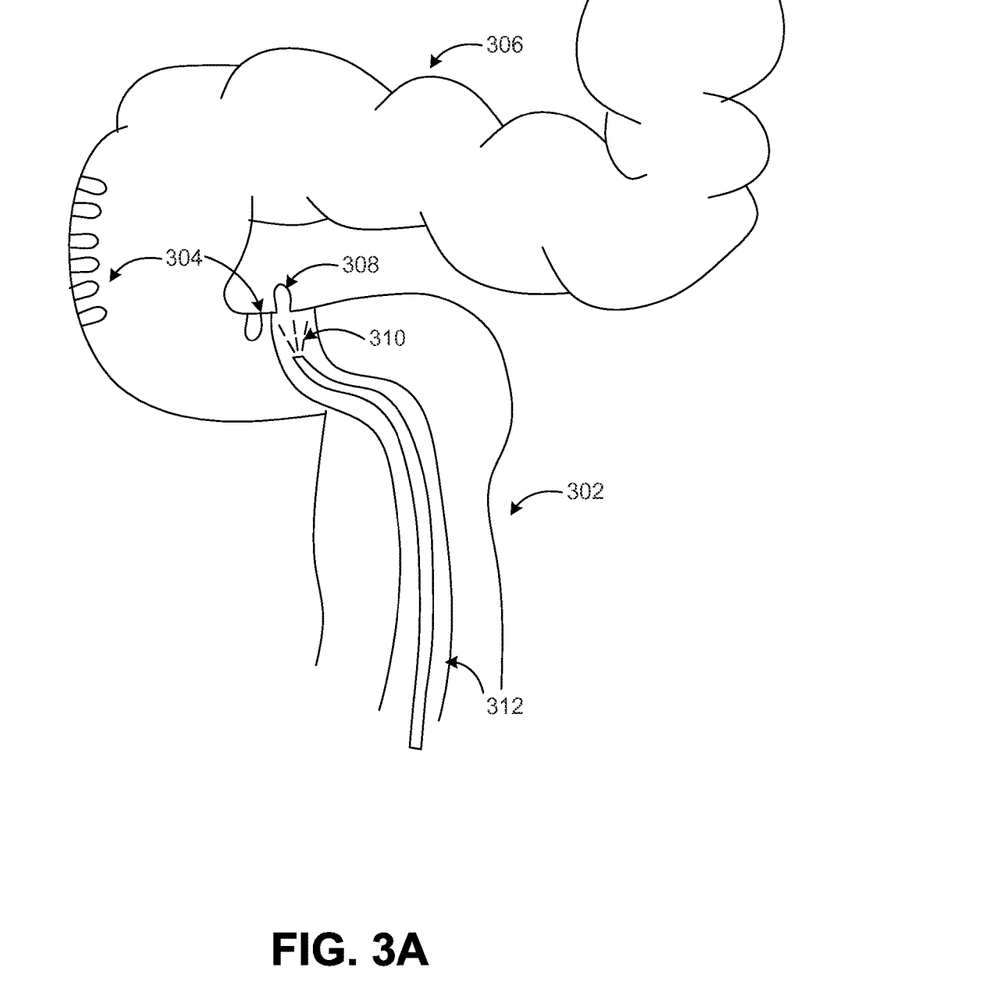
FIGS. 3A and 3B illustrate example methods of inverting diverticula.

FIGS. 3A and 3B illustrate example methods of inverting diverticula, arranged in accordance with at least some embodiments as described herein. As illustrated in FIG. 3A, a vacuum technique may be employed for inverting diverticula to cause the diverticula to extend into an interior space of the colon 306 as inverted diverticula 304. The vacuum technique may involve identifying an inflamed diverticulum 308 tier removal, inserting a delivery tube 312 into the colon 306, and applying a vacuum 310 to the inflamed diverticulum 308 in order to invert or turn the inflamed diverticulum 308 inside out. The delivery tube 312 may be inserted employing an endoscopic procedure into the colon 306 through the rectum 302 for providing access to the interior space of the intestines. The delivery tube 312 may be positioned at a location near the inflamed diverticulum 308. Once in position near the inflamed diverticulum 308, the delivery tube 312 may provide access to the inflamed diverticulum 308 by the vacuum 310. The vacuum 310 may be inserted through the delivery tube 312 and positioned over the inflamed diverticulum 308. The vacuum 310 may be controlled by a physician outside the body to apply suction to the inflamed diverticulum 308, thereby inverting the inflamed diverticulum 308 to extend into the interior space of the colon 306. In an example embodiment, the amount of diverticulum tissue to be inverted may be controlled by varying the diameter of the vacuum 310 such that the amount of tissue drawn into the vacuum is regulated by the diameter of the vacuum 310. Regulation of the amount of tissue that becomes inverted may help ensure that the appropriate amount of tissue is inverted for promoting healing of the mucosal walls and necrosis of the inverted diverticulum.

Figure 3B:
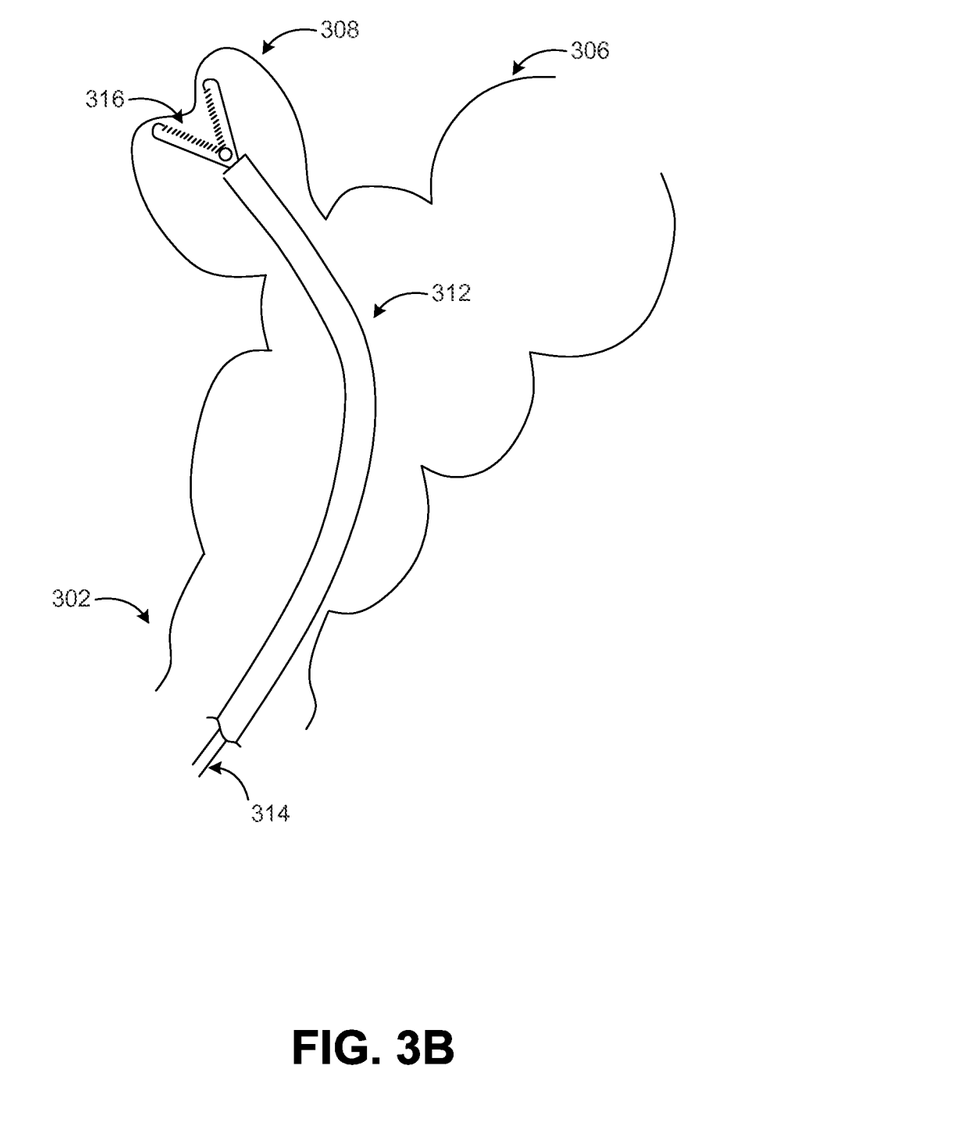

As illustrated in FIG. 3B, a mechanical technique may also be employed fir inverting diverticula 304 to cause the diverticula 304 to extend into the interior space of the colon 306. The mechanical technique may involve inserting the delivery tube 312 into the colon 306 position near the inflamed diverticulum 308. A mechanical tool 314 may be inserted through the delivery tube 312 to manually grasp the diverticulum 308 and manually invert or turn the inflamed diverticulum 308 inside out. In an example embodiment, the amount of diverticulum tissue to be inverted may be controlled by manually controlling the amount of tissue grasped by the mechanical tool 314.

In another embodiment, additional techniques may be employed for inverting the inflamed diverticulum 308 into the interior space of the colon 306. An example technique may include employing a hydrophilic membrane for creating an osmotic force to invert the inflamed diverticulum 308 into the interior space of the colon 306. For example, a saline solution may be exposed to the diverticulum and a gradient may be created causing water to be removed from the tissue protrusion and causing the tissue protrusion to become inverted.

Figure 4A:
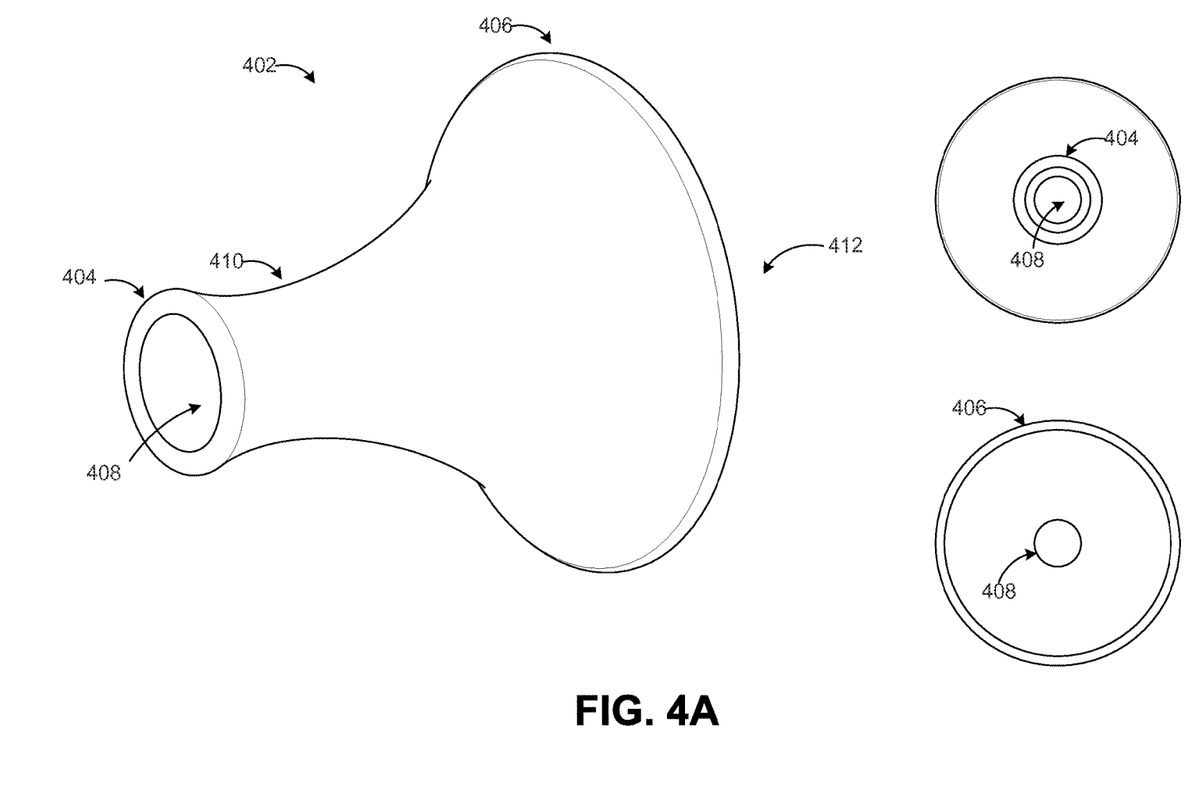
FIGS. 4A and 4B illustrate an example diverticula removal device having a tapered shape.

FIGS. 4A and 4B illustrate an example diverticula removal device having a tapered shape, arranged in accordance with at least some embodiments as described herein. As illustrated in FIG. 4A, an example diverticula removal device may be a tube 402 having a tapered shape with a changing inner diameter from a first opening 408 to a second inner opening 412 of the tube 402 which may be placed over an inverted diverticulum. In an example configuration, the tube 402 may form a trumpet bell shape such that the first opening 408 has a first inner diameter 404, and the inner diameter decreases to a narrowest inner diameter 410, and then increases to a widest inner diameter 406 at second opening 412. In the trumpet bell shape, the tube 402 may resemble two cones having a common narrowest diameter attached to each other at the portion of each cone having the narrowest diameters.

In an example embodiment, the tube 402 may be placed over an inverted diverticulum to cause necrosis of the diverticulum at the point having the narrowest diameter. The opening having the widest diameter may be placed over the diverticulum closest to the colon wall for promoting healing of the colon tissue, and the opening having the narrowest diameter may be positioned away from the colon wall near a tip of the inverted diverticulum for promoting necrosis and removal of the diverticulum.

In an example embodiment, the narrowest diameter may be in a range from about a range from about 0.5 mm to about 10 mm. The widest diameter may be in a range from about a range from about 1 mm to about 12 mm. Additionally, the tube may have a length in a range from about 3 mm to about 10 mm.

In another example embodiment, the tube 402 may be composed from a flexible material such as silicon. In another embodiment, tube 402 may be composed from a polymer material such as one or more of polyethylene, polypropylene, polyester, polyurethane, polystyrene, polysulfone and/or polyethersulfone. Additionally the tube 402 may be composed from a bio-absorbable material. Further the tube 402 may be composed from a bio-degradable material for enabling the tube 402 to be removed through a process of biodegradation. Further, tube 402 may be composed from one or more of stainless steel and nickel titanium alloy.

In another embodiment, an inner surface of the tube 402 may be texturized for facilitating keeping the tube in position over the inverted diverticulum. The inner surface of the tube 402 may be texturized in a unidirectional manner, such that the tube 402 may easily and smoothly slide over the inverted diverticulum towards the colon wall, and a mechanical friction may be induced for inhibiting the tube 402 from sliding off of the diverticulum and away from the colon wall.

Figure 4B:
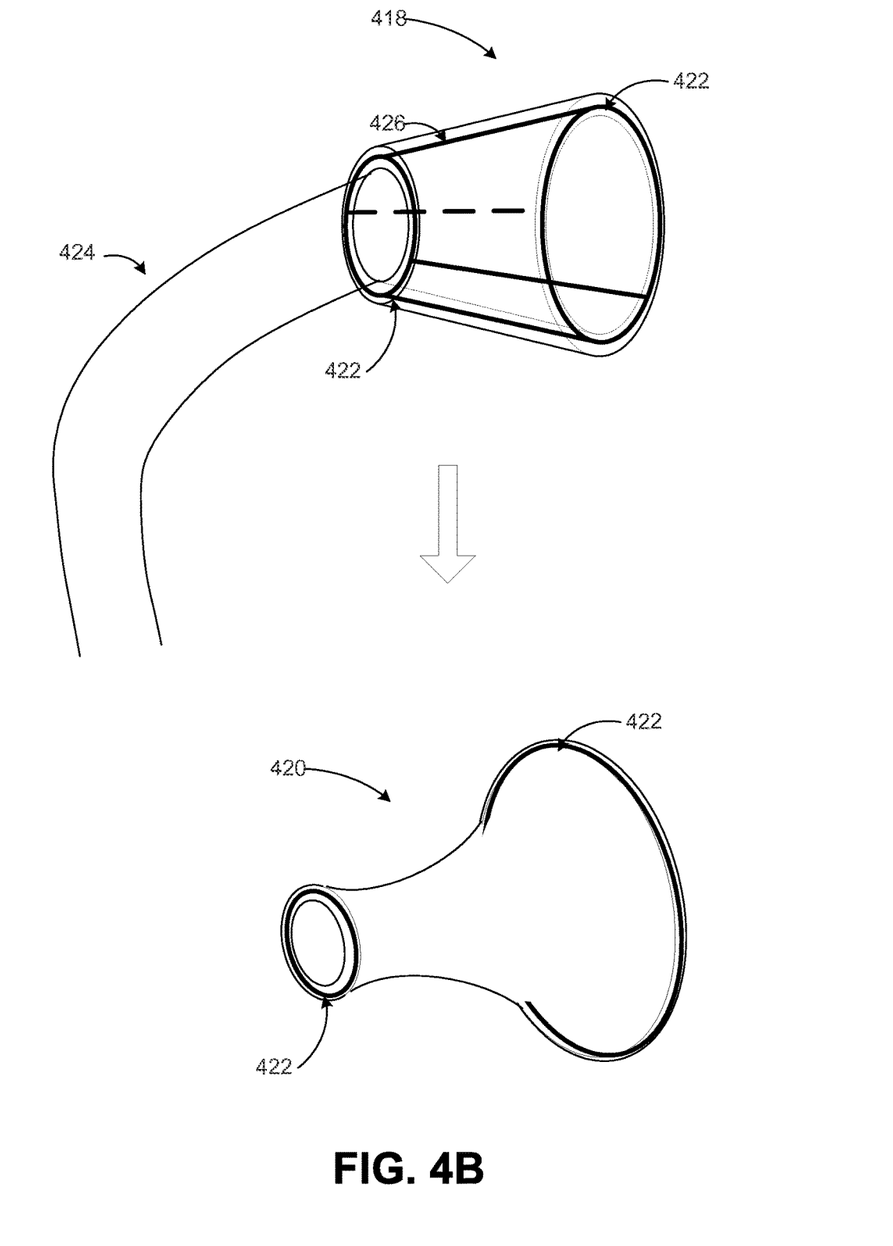

In another example embodiment, as illustrated in FIG. 4B, rigid reinforcement members 426, 422 may be integrated with the diverticula removal device, or the tube, to support and maintain the diverticula removal device in an un-deployed shape 418 and a deployed shape 420. The reinforcement members 426, 422 maintaining the un-deployed shape 418 may aid in positioning the tube over inverted diverticula tissue. Additionally, the reinforcement members 426, 422 maintaining the un-deployed shape 418 may enable the tube to be utilized as a nozzle with a vacuum device 424, or suction tube, to position the tube over diverticula tissue to invert the diverticula. The reinforcement members 426, 422 may prevent collapse of the tube while the diverticulum tissue is suctioned and inverted. After a desired amount of the diverticulum tissue has been inverted, the reinforcement members 426, 422 may be removed, and the tube may deploy into the deployed shape in which at least a portion of the inner diameter may decrease. Deploying into the deployed shape 420 may be initiated by applied suction from the vacuum device 424 as a pressure gradient is initiated by the suction.

In an example embodiment, the un-deployed shape 418 may be a tapered shape with the inner diameter steadily changing from the first opening to the second opening, and in the deployed shape 420, the tube may form a trumpet bell shape as previously described. One or more reinforcement members 426 may be placed along a length of the tube. Additionally one or more reinforcement members 422 may be placed around a circumference of each of the first and second openings to maintain the openings at a constant diameter. The reinforcement members 422, 426 may be positioned either externally or internally on the tube. The reinforcement members may be composed of a polymer, stainless steel, and/or nickel titanium alloy.

Figure 5A:
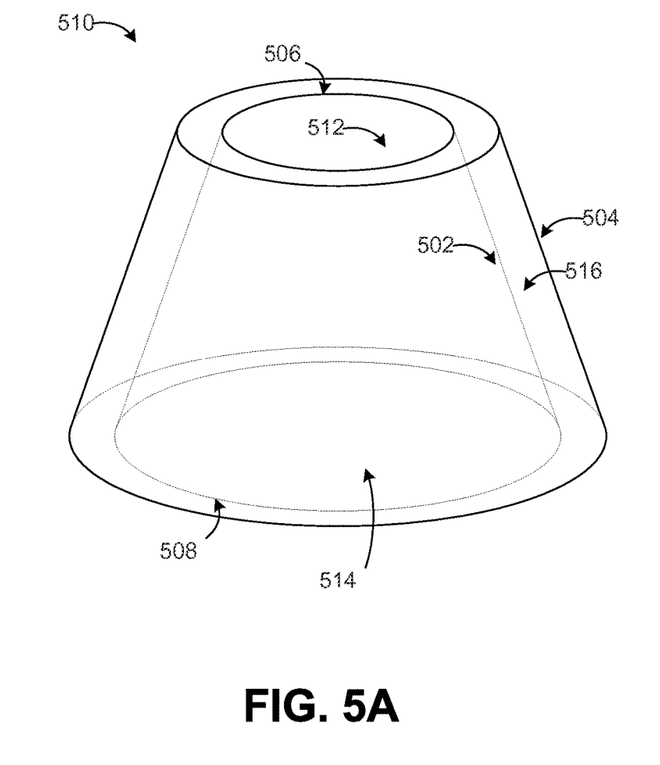
FIGS. 5A and 5B illustrate example diverticula removal devices.

FIGS. 5A and 5B illustrate example diverticula removal devices, arranged in accordance with at least some embodiments as described herein. As illustrated in FIG. 5A, in another example configuration, the diverticula removal device may be a tube 510 that forms a frusto-conical shape. When the tube 510 forms the frusto-conical shape, a first opening 512 may have a narrowest inner diameter 506, and a second opening 514 may have a widest inner diameter 508. In an example embodiment, the walls 516 of the tube 510 may have an even thickness, such that the inner diameter 502 and the outer diameter 504 may change proportionately with respect to each other from the first opening 512 to the second opening 514. Additionally, in an example embodiment, the first opening 512 and the second opening 514 may have a substantially rounded or circular cross sectional shape.

Figure 5B:
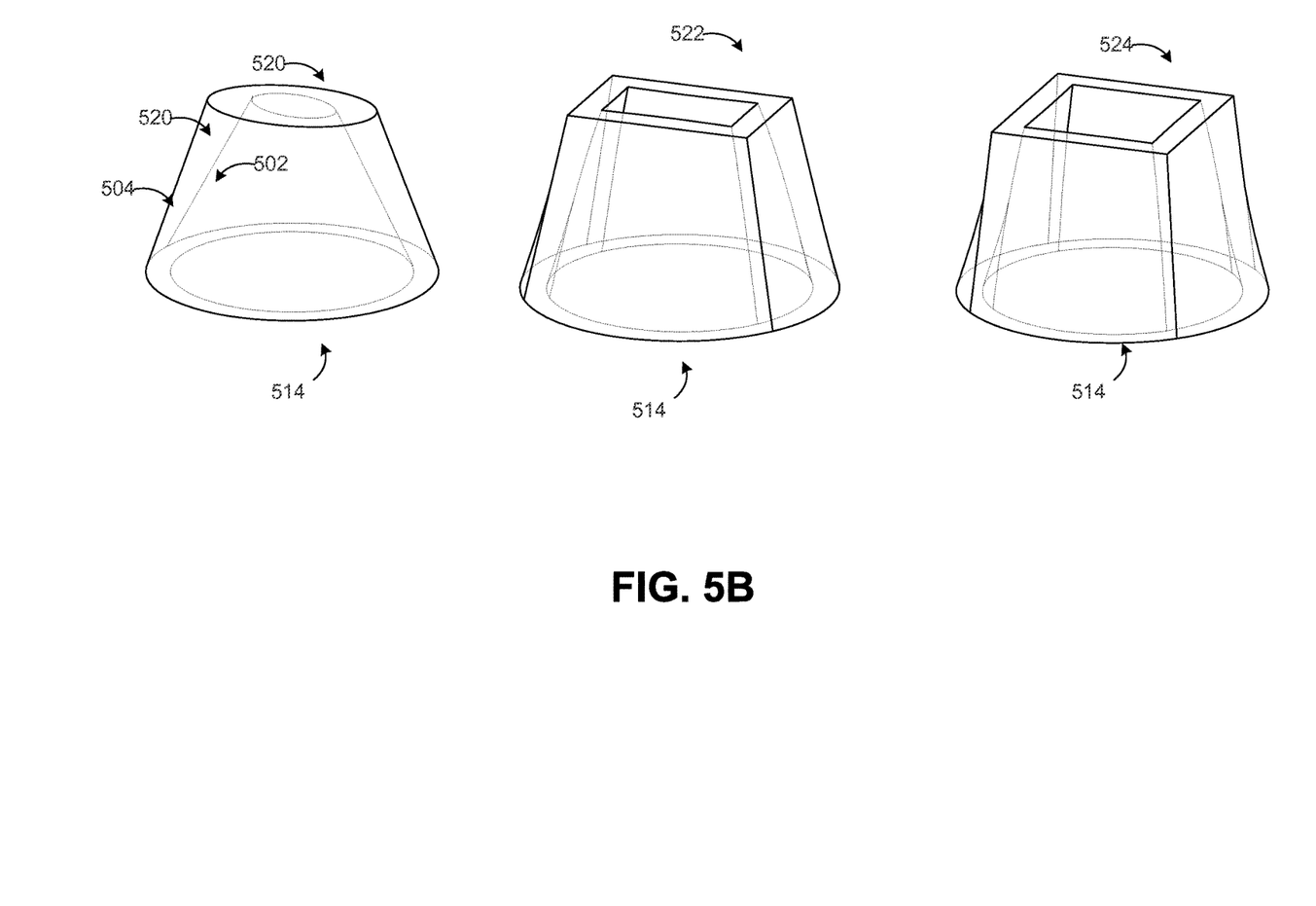

As further illustrated in FIG. 5B, the first opening 512 and the second opening 514 may have other polygonal shapes, such as rectangular 522, oval 520, and square 524 as some examples. Additionally, in another example configuration, the walls 520 of the tube 510 may have a graduated thickness, such that the inner diameter 502 and the outer diameter 504 may change at varying diameter values from the first opening 512 to the second opening 514.

Figure 6:
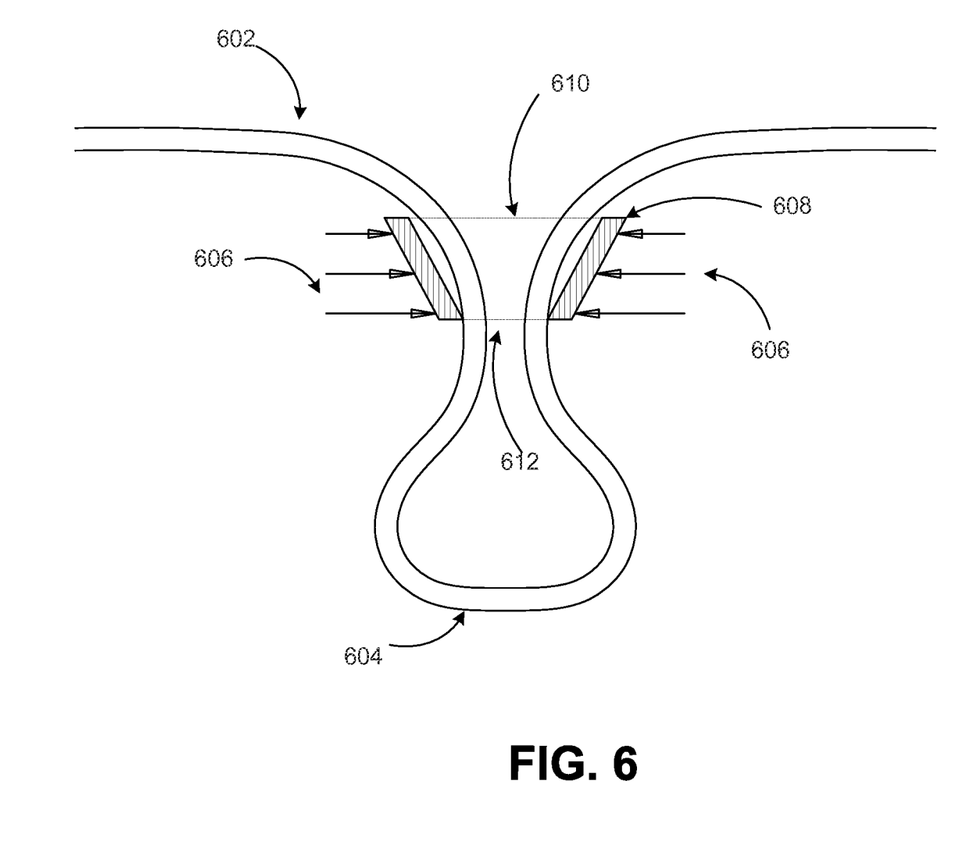
FIG. 6 illustrates placement of a diverticula removal device over an inverted diverticula in the intestines.

FIG. 6 illustrates placement of a diverticulum removal device over an inverted diverticulum in the intestines, arranged in accordance with at least some embodiments as described herein. A tube 608 in accordance with embodiments as described herein may be placed over an inverted diverticulum 604 to promote removal of the inverted diverticulum 604 and healing of the remaining muscle of the colon 602 wall. The tube 608 may be slid over the inverted diverticulum 604 with a widest opening 610 positioned closest to the colon 602 and a narrowest opening 612 positioned distally from the colon 602 near a tip of the inverted diverticulum 604. The narrowest opening 612 may be a necrotic end configured to cause necrosis of the inverted diverticulum 604, and the widest opening 610 may be a healing end configured to promote healing of the muscle walls of the colon 602.

In an example embodiment, when the tube 608 is in position over the inverted diverticulum 604 with the widest opening 610 near the colon wall, the inverted diverticulum 604 may be pinched together within the narrowest opening 612 of the tube. A graduated pressure gradient 606 may be induced from the widest opening 610 to the narrowest opening 612, such that the pressure applied to the inverted diverticulum 604 increases from the widest opening 610 to the narrowest opening 612. At the narrowest opening 612 of highest pressure, the opposing muscularis mucosal walls of the inverted diverticulum 604 may be pinched together to induce necrosis of the inverted diverticulum 604 by blocking blood flow with the diverticulum tissue. Additionally, as the pressure gradient 606 gradually decreases along the widening diameter of the tube, a non-necrosal mucosal contact region may be created which may promote healing of the mucosal walls of the colon 602.

Figure 7:
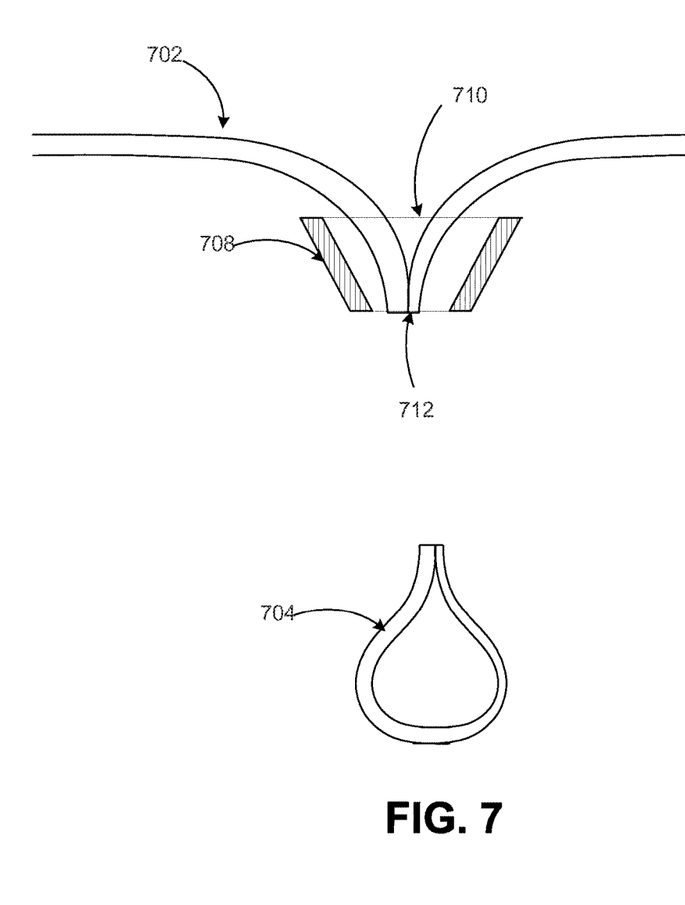
FIG. 7 illustrates a removed diverticula from the intestinal wall.

FIG. 7 illustrates a removed diverticulum from the intestinal wall, arranged in accordance with at least some embodiments as described herein. The tube 708 may be positioned over an inverted diverticulum 704 such that a widest opening 710 may be positioned closest to the colon 702 and a narrowest opening 712 may be positioned distally from the colon 702 around a portion of the inverted diverticulum 704. As previously discussed, a graduated pressure gradient may be applied to the inverted diverticulum 704 that increases from the widest opening 710 to the narrowest opening 712. At the narrowest opening 712 having the highest pressure, the opposing muscularis mucosal walls of the inverted diverticulum 704 may be pinched together, and blood flow may be blocked within the muscularis mucosal walls of the inverted diverticulum 704.

When the blood flow is blocked, the inverted diverticulum 704 may become necrosed at the point within narrowest opening of the tube where there is no blood flow. When the diverticulum becomes necrosed, the inverted diverticulum 704 may separate from the remaining mucosa tissue of the colon 702 such that the inverted diverticulum 704 may be detached from the colon 702. The detached diverticulum may subsequently pass through the colon for removal through a natural body process. After the diverticulum has been removed, the tube 708 may also pass through the intestines for removal through a natural body process. In another embodiment, the tube 708 may be composed from a bio-absorbable material, and after the diverticulum has been removed, the tube 708 may be naturally absorbed within the body. Additionally, the tube 708 may be composed from a bio-degradable material and removed through a process of biodegradation.

Figure 8:
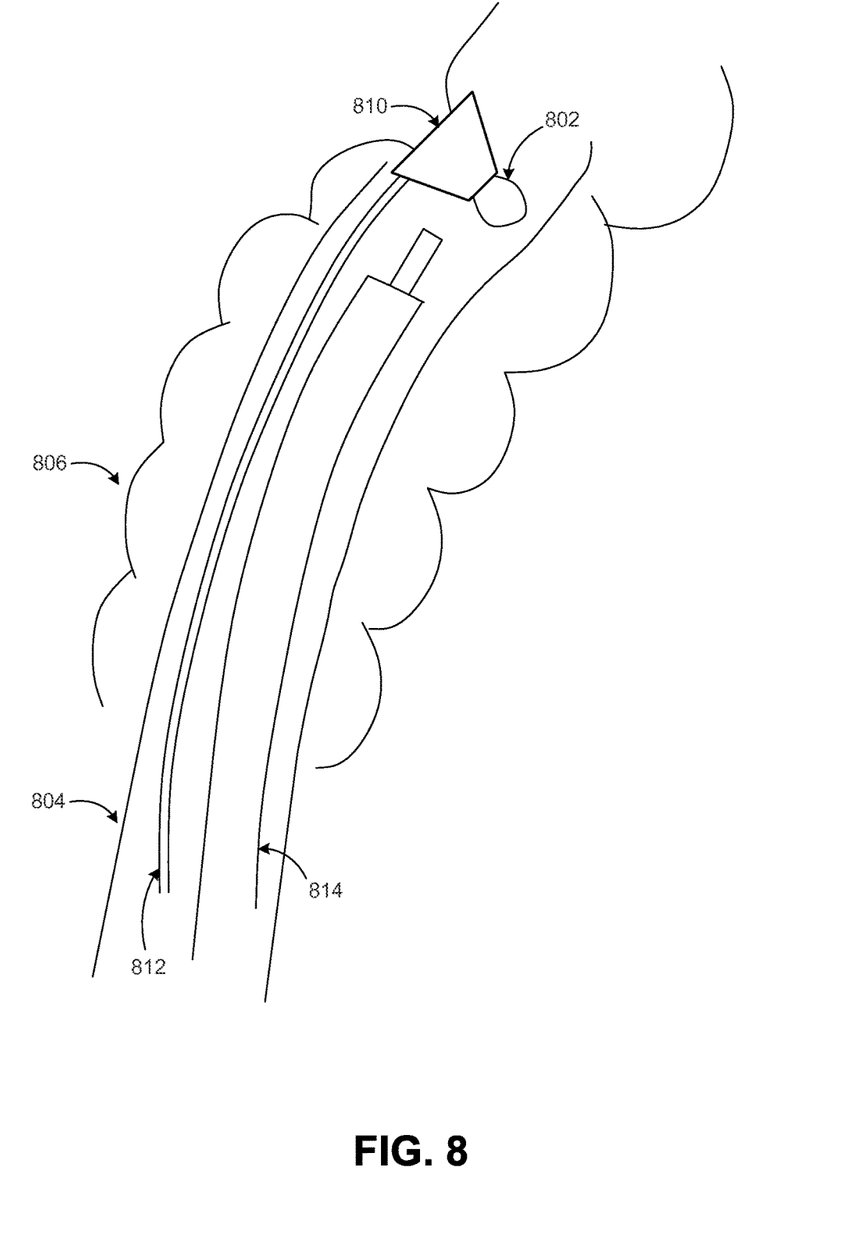
FIG. 8 illustrates delivery and placement of a diverticula removal device employing endoscopic tools, all arranged in accordance with at least some embodiments as described herein.

FIG. 8 illustrates delivery and placement of a diverticulum removal device employing endoscopic tools, arranged in accordance with at least some embodiments as described herein. A diverticulum removal device 810 may be positioned over an inverted diverticulum 802 employing an endoscopic procedure. During the endoscopic procedure, a delivery tube 804 may be initially inserted into the colon 806 for providing access to the interior space of the intestines and/or colon. A tool 814, such as a vacuum or mechanical tool, may then be inserted through the delivery tube 804 for inverting the diverticulum into the interior space of the colon. Subsequently, a guiding tool 812 may be utilized for inserting the diverticulum removal device 810 into the colon and sliding the diverticulum removal device 810 over the inverted diverticulum 802. When the diverticulum removal device 810 is in position over the inverted diverticulum 802, a widest portion of the diverticulum removal device 810 may be oriented near the colon wall, and a narrowest portion of the diverticulum removal device 810 may be oriented around a distal end of the inverted diverticulum 802 away from the colon wall for promoting necrosis and removal of the inverted diverticulum.

While embodiments have been discussed above using specific examples, components, and configurations, they are intended to provide a general guideline to be used for—providing a tissue removal device for removing tissue protrusions extending from a wall of intestines. These examples do not constitute a limitation on the embodiments, which may be implemented using other components, modules, and configurations using the principles described herein. Furthermore, actions discussed above may be performed in various orders, especially in an interlaced fashion.

According to some embodiments, the present disclosure describes a tissue removal device for removing tissue protrusions extending from a wall of intestines. The tissue removal device may include a tube including a first opening having a first diameter, and a second opening having a second diameter, the tube being configured to slide over a tissue protrusion such that the first opening may be adjacent to the wall of the colon and the tissue protrusion passes through the second opening, wherein the tube may have a tapered shape extending from the first opening to the second opening.

According to some embodiments, the tube may form a frusto-conical shape. An inner diameter of the tube may decrease from a first diameter at the first opening to a third diameter between the first and second openings and then increase from the third diameter to a second diameter at the second opening. The tube may form a trumpet bell shape.

According to some embodiments, a wall of the tube may be configured to have a substantially even thickness such that the inner diameter changes proportionately with an outer diameter. A wall of the tube may be configured to have a graduated thickness. At least one of the first opening and the second opening have a substantially rounded cross sectional shape. At least one of the first opening and the second opening may have a polygonal cross sectional shape.

According to some embodiments, the tube may be composed of a polymer material. The polymer material may include one or more of polyethylene, polypropylene, polyester, polyurethane, polystyrene, polysulfone and/or polyethersulfone. The tube may be composed of a bio-absorbable material to enable the tube to be naturally removed. The tube may be composed of a metal and/or an alloy. The metal may be selected from the group consisting of: one of stainless steel and nickel titanium alloy.

According to some embodiments, the tissue protrusions may be inverted to extend into an interior space of the intestines employing an endoscopic procedure. The tube may be configured to be delivered to a location of the tissue protrusions employing the endoscopic procedure. A portion of the tube having a narrowest diameter may be configured to cause opposing muscularis mucosal walls of the tissue protrusions to bond to promote necrosis and removal of the tissue protrusions.

According to some embodiments, the tube may be configured to cause a pressure gradient such that an applied pressure decreases from the portion of the tube having the narrowest diameter to the first opening having the widest diameter. The tube may be configured to slide over a tissue protrusion located within the colon. One or more reinforcement members may be integrated with the tube at one or more of along a length of the tube, at the first opening, and at the second opening of the tube.

According to other embodiments, the present disclosure also describes a method of removing tissue protrusions extending from a wall of intestines. The method may include inverting one or more tissue protrusions extending from the wall of the intestines such that the tissue protrusions extend into an interior space of the intestines, providing a tube configured to slide over a tissue protrusion such that a first opening of the tube having a first inner diameter may be adjacent to the wall of the intestines, and the tissue protrusion passes through a second opening of the tube having a second inner diameter, wherein the tube may have a tapered shape extending from the first opening to the second opening; and causing opposing muscularis mucosal walls of the tissue protrusion located within the second opening to bond for promoting necrosis and removal of the tissue protrusions.

According to some embodiments, the tube may form a frusto-conical shape. The method may also include configuring an inner diameter of the tube to decrease from the first inner diameter at the first opening to a third inner diameter between the first and second openings and then increase from the third inner diameter to the second inner diameter at the second opening. The method may also include configuring the third inner diameter to be a narrowest diameter of the tube, such that the tube forms a trumpet bell shape, and causing the opposing muscularis mucosal walls of the tissue protrusion located within the third inner diameter to bond for promoting necrosis and removal of the tissue protrusions.

According to other embodiments, the method may also include configuring a wall of the tube to have an even thickness such that the inner diameter changes proportionately with an outer diameter. The method may also include configuring a wall of the tube to have a graduated thickness. The method may also include configuring at least one of the first opening and the second opening to have a substantially rounded cross sectional shape. The method may also include configuring at least one of the first opening and the second opening to have a polygonal cross sectional shape.

According to further embodiments, the method may also include composing the tube from a polymer material. The method may also include composing the tube from one or more of polyethylene, polypropylene, polyester, polyurethane, polystyrene, polysulfone and/or polyethersulfone. The method may also include composing the tube from a bio-absorbable material. The method may also include composing the tube from one of stainless steel and nickel titanium alloy.

According to yet other embodiments, the method may also include inverting the tissue protrusions into the interior space of the intestines employing an endoscopic procedure. The method may also include inverting the tissue protrusions into the interior space of the intestines employing a vacuum tool. The method may also include employing a mechanical tool for grasping the tissue protrusion and manually inverting the tissue protrusions into the interior space of the intestines. The method may also include employing a hydrophilic membrane for creating an osmotic force for inverting the tissue protrusions into the interior space of the intestines.

According to other embodiments, the method may also include delivering the tube to a location of the tissue protrusions employing the endoscopic procedure. The method may also include causing a pressure gradient such that an applied pressure decreases from the portion of the tube having a narrowest inner diameter to the first opening having a widest inner diameter. The method may also include integrating one or more reinforcement members with the tube in an un-deployed shape at one or more of: along a length of the tube, at the first opening, and at the second opening of the tube, delivering the tribe in the un-deployed shape to a location of the tissue protrusion, and removing at least one of the reinforcement members to cause the tube to deploy into a deployed shape to promote necrosis and removal of the tissue protrusion.

According to further embodiments, the present disclosure describes a system for removing tissue protrusions extending from a wall of intestines. The system may include a surgical delivery tool for providing access to an interior space of the intestines, and a tube including a first opening having a first diameter, and a second opening having a second diameter, the tube being configured to slide over a tissue protrusion such that the first opening may be adjacent to the wall of the colon and the tissue protrusion passes through the second opening, wherein the tube may have a tapered shape extending from the first opening to the second opening.

According to some embodiments, the tube may form a frusto-conical shape. The tube may also form a trumpet bell shape. One or more reinforcement members may be integrated with the tube at one or more of: along a length of the tube, at the first opening, and at the second opening of the tube. One or more reinforcement members may be integrated with the tube on one of: an external surface or an internal surface.

The tissue protrusions may be inverted into the interior space of the intestines employing an endoscopic procedure. The tube may be guided into the interior space of the intestines employing the endoscopic procedure. The tube may be deployed into position over the inverted tissue protrusion with the first opening may be adjacent to the wall of the colon and an elongated portion of the tissue protrusion passing through the second opening.

According to other embodiments, a pressure gradient may be caused such that an applied pressure decreases from the portion of the tube having a narrowest diameter to the first opening having a widest diameter.

According to yet other embodiments, the portion of the tube having the narrowest diameter may be configured to cause opposing muscularis mucosal walls of the tissue protrusions to bond for promoting necrosis of the tissue protrusions.

According to some embodiments, the necrosed tissue protrusions may be configured to pass through the intestines for removal through a natural body process. After the necrosed tissue protrusions are removed from the intestines, the tube may be configured to pass through the intestines for removal through a natural body process. After the necrosed tissue protrusions are removed from the intestines, the tube may be configured to be naturally absorbed within the body.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communication link, a wireless communication link, etc).

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A tissue clamping device for removing tissue protrusions extending from a wall of intestines, the tissue clamping device comprising:
a tube including a first opening having a first diameter, a second opening having a second diameter, and one or more removable reinforcement members at one or more of: along a length of the tube, at the first opening of the tube, and at the second mating of the tube for maintaining the tissue clamping device in a frusto-conical shape and a trumpet bell shape, the tube being configured to be in the frusto-conical shape to slide over a tissue protrusion such that the first opening is adjacent to the wall of a colon and the tissue protrusion passes through the second opening, wherein the tube has a tapered shape extending from the first opening to the second opening, and wherein the tube is configured to form the trumpet bell shape to cause a pressure gradient such that an applied pressure decreases from a portion of the tube having a narrowest diameter to a portion of the tube having a widest diameter.

2. The tissue clamping device of claim 1, wherein an inner diameter of the tube decreases from a first diameter at the first opening to a third diameter between the first opening and the second opening and then increases from the third diameter to a second diameter at the second opening.

3. The tissue clamping device of claim 2, wherein a wall of the tube is configured to have a substantially even thickness such that the inner diameter changes proportionately with an outer diameter.

4. The tissue clamping device of claim 2, wherein a wall of the rube is configured to have a graduated thickness.

5. The tissue clamping device of claim 1, wherein the tissue protrusions are inverted to extend into an interior space of the intestines employing an endoscopic procedure.

6. The tissue clamping device of claim 5, wherein the tube is configured to be delivered to a location of the tissue protrusions employing the endoscopic procedure.

7. The tissue clamping device of claim 6, wherein a portion of the tube having a narrowest diameter is configured to cause opposing muscularis mucosal walls of the tissue protrusions to bond to promote necrosis and removal of the tissue protrusions.

8. A method of removing tissue protrusions extending from a wall of intestines, the method comprising:
inverting one or more tissue protrusions extending from the wall of the intestines such that the tissue protrusions extend into an interior space of the intestines;

providing a tube having one or more removable reinforcement members at one or more of along a length of the tube, at the first opening, and at the second opening of the tube for maintaining the tissue clamping device in a frusta-conical shape and a trumpet bell shape, wherein the tube is configured to be in the frusto-conical shape to slide over a tissue protrusion such that a first opening of the tube having a first inner diameter is adjacent to the wall of the intestines, and the tissue protrusion passes through a second opening of the tube having, a second inner diameter, wherein the tube has a tapered shape extending from the first opening to the second opening;

causing a pressure gradient by configuring the tube to be in the trumpet bell shape such that an applied pressure decreases from a portion of the tube having a narrowest inner diameter to the first opening having, a widest inner diameter; and causing opposing muscularis mucosal walls of the tissue protrusion located within the second opening to bond for promoting necrosis and removal of the tissue protrusions.

9. The method of claim 8, further comprising:
configuring at least one of the first opening and the second opening to have one of: a substantially rounded cross sectional shape or a polygonal cross sectional shape.

10. The method of claim 8, further comprising:
composing the tube from a polymer material selected from one or more of polyethylene, polypropylene, polyester, polyurethane, polystyrene, polysulfone and/ or polyethersulfone.

11. The method of claim 8, further comprising:
unidirectionally texturizing a inner surface of the tube to induce mechanical friction against the muscularis mucosal walls of the tissue protrusion in a direction away from a colon wall.

12. The method of claim 8, further comprising:
composing the tube from a bio-absorbable material.

13. The method of claim 8, further comprising:
composing the tube from one of stainless steel and nickel titanium alloy.

14. The method of claim 8, further comprising:
inverting the tissue protrusions into the interior space of the intestines employing one or more of: a vacuum tool, a mechanical tool for grasping the tissue protrusion and manually inverting the tissue protrusions, or a hydrophilic membrane for creating an osmotic force to invert the tissue protrusions.

15. The method of claim 8, further comprising:
sliding the tube over a tissue protrusion; and removing at least one of the reinforcement members to cause the tube to deploy into a shape to promote necrosis and removal of the tissue protrusion.

16. A system for removing tissue protrusions extending from a wall of intestines, the system comprising:
a surgical delivery tool for providing access to an interior space of the intestines; and
a tube including a first opening having a first diameter, and a second opening having a second diameter, one or more removable reinforcement members at one or more of: along a length of the tube, at the first opening of the tube, and at the second opening of the tube for maintaining the tissue clamping device in a frusto-conical shape and a trumpet bell shape, the tube being configured to be in the frusto-conical shape to slide over a tissue protrusion such that the first opening is adjacent to the wall of a colon and the tissue protrusion passes through the second opening, wherein the tube has a tapered shape extending from the first opening to the second opening, and wherein the tube is configured to form the trumpet bell shape to cause a pressure gradient such that an applied pressure decreases from a portion of the tube having a narrowest diameter to the first opening having a widest diameter.

17. The system of claim 16, wherein the tube is configured to slide over an inverted tissue protrusion with the first opening adjacent to the wall of the colon and an elongated portion of the tissue protrusion passing through the second opening.

18. The system of claim 16, wherein a portion of the tube having the narrowest diameter is configured to cause opposing muscularis mucosal walls of the tissue protrusions to bond for promoting necrosis of the tissue protrusions.

19. The system of claim 18, wherein the tube is configured to pass through the intestines for removal through a natural body process.

20. The system of claim 18, wherein the tube is configured to be naturally absorbed within the body.

* * * * *

UNITED STATES PATENT AND TRADEMARK OFFICE
CERTIFICATE OF CORRECTION

PATENT NO. : 9,848,884 B2
APPLICATION NO. : 14/125929
DATED : December 26, 2017
INVENTOR(S) : Bertollo et al.

Page 1 of 2

It is certified that error appears in the above-identified patent and that said Letters Patent is hereby corrected as shown below:

On the Title Page

In Item (57), under "Abstract", in Column 2, Line 6, delete "device run be" and insert -- device may be --, therefor.

In the Specification

In Column 2, Line 60, delete "inter cilia," and insert -- inter alia, --, therefor.

In Column 3, Line 59, delete "308 tier removal," and insert -- 308 for removal, --, therefor.

In Column 4, Line 19, delete "employed fir" and insert -- employed for --, therefor.

In Column 8, Line 28, delete "more of along" and insert -- more of: along --, therefor.

In Column 9, Line 33, delete "tribe in" and insert -- tube in --, therefor.

In Column 10, Line 49, delete "link, etc)." and insert -- link, etc.). --, therefor.

In the Claims

In Column 12, Line 28, in Claim 1, delete "second mating" and insert -- second opening --, therefor.

In Column 12, Line 51, in Claim 4, delete "the rube is" and insert -- the tube is --, therefor.

In Column 13, Line 2, in Claim 8, delete "more of along" and insert -- more of: along --, therefor.

In Column 13, Line 5, in Claim 8, delete "frusta-conical" and insert -- frusto-conical --, therefor.

In Column 13, Line 11, in Claim 8, delete "having, a" and insert -- having a --, therefor.

Signed and Sealed this
Seventh Day of August, 2018

Andrei Iancu
*Director of the United States Patent and Trademark Office*

CERTIFICATE OF CORRECTION (continued)
U.S. Pat. No. 9,848,884 B2

In Column 13, Line 17, in Claim 8, delete "having, a" and insert -- having a --, therefor.

In Column 13, Line 33, in Claim 11, delete "unidirectionally texturizing a inner" and insert -- unidirectional texturizing an inner --, therefor.